(12) United States Patent
Verstegen et al.

(10) Patent No.: US 8,395,704 B2
(45) Date of Patent: Mar. 12, 2013

(54) FLUID TRANSMISSION THROUGH A VISUAL DISPLAY PANEL

(75) Inventors: Emile Johannes Karel Verstegen, Eindhoven (NL); Dirkjan Bernhard Van Dam, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1193 days.

(21) Appl. No.: 12/092,713

(22) PCT Filed: Nov. 7, 2006

(86) PCT No.: PCT/IB2006/054137
§ 371 (c)(1),
(2), (4) Date: May 6, 2008

(87) PCT Pub. No.: WO2007/054887
PCT Pub. Date: May 18, 2007

(65) Prior Publication Data
US 2008/0289704 A1    Nov. 27, 2008

(30) Foreign Application Priority Data

Nov. 10, 2005 (EP) .................... 05110620

(51) Int. Cl.
*H04N 7/00* (2011.01)
*F15B 13/00* (2006.01)
*A61L 9/00* (2006.01)
*A62B 7/08* (2006.01)
*H04L 12/58* (2006.01)
*G06K 7/10* (2006.01)
*G05D 7/00* (2006.01)
*G05D 11/02* (2006.01)
*G05D 11/16* (2006.01)

(52) U.S. Cl. ............ 348/552; 137/560; 422/4; 422/124; 455/412.1; 235/462.13; 700/285

(58) Field of Classification Search .................. None
See application file for complete search history.

(56) References Cited

U.S. PATENT DOCUMENTS

| | | | | |
|---|---|---|---|---|
| 4,629,604 A | * | 12/1986 | Spector | 422/124 |
| 5,724,256 A | * | 3/1998 | Lee et al. | 700/285 |
| 2001/0008611 A1 | * | 7/2001 | Budman | 422/4 |
| 2003/0029918 A1 | * | 2/2003 | Leanheart et al. | 235/462.13 |
| 2004/0214551 A1 | * | 10/2004 | Kim | 455/412.1 |

FOREIGN PATENT DOCUMENTS

| | | |
|---|---|---|
| FR | 2841081 A1 | 12/2003 |
| GB | 807615 | 1/1959 |
| JP | 10085315 | 4/1998 |
| JP | 10123981 A | 5/1998 |
| JP | 2002123206 A | 4/2002 |
| JP | 2005000289 A | 1/2005 |
| JP | 2005077529 A | 7/2005 |
| WO | WO2005091257 A1 | 9/2005 |

* cited by examiner

*Primary Examiner* — Jefferey Harold
*Assistant Examiner* — Sean Haiem

(57) ABSTRACT

A visual display panel (1) comprising: a front face (3); an array of optical display elements, a plurality of fluid flow conduits, each conduit extending through the panel from an aperture on the front face; and a manifold (32) in fluid communication with one or more of the plurality of fluid flow conduits, the manifold having one or more manifold inlets (38) fluidly coupled to a fluid pump (33) for displacing fluid through the conduits.

14 Claims, 6 Drawing Sheets

FLUID TRANSMISSION THROUGH A VISUAL DISPLAY PANEL

The invention relates generally to visual display panels associated with odour or gas distribution systems.

Current display technologies usually provide both visual and audio outputs. In the prior art, there have been proposals to include means for emission of odours in conjunction with visual and audio outputs. UK patent 807,615, for example, discloses an apparatus for causing emission of appropriate odours in synchronised relation with motion pictures. US 2004/0214551 discloses a digital mobile telephone with multimedia data reproducing and outputting means including a loudspeaker, a display screen and an odour-emitting device. Such proposals have envisaged provision of an output odour emission mechanism that is distinct and separate from the display element itself.

There is a need, therefore, for a technology which can enhance the existing audiovisual experience, preferably in an integrated fashion and preferably with the ability for the user to interact by means such as touch.

It is an object of the invention to provide a visual display panel adapted for the active transmission of fluids therethrough.

It is a further object of the invention to provide an improved immersive experience for a user of a visual display panel, in which smell is integrated with an audiovisual experience.

It is a further object of the invention to provide an interactive element to a visual display panel, in which a touch sensitive function is provided together with means for emitting smells from the visual display panel.

Some or all of the above objects may be achieved with embodiments of the invention.

According to a first aspect, the present invention provides a visual display panel comprising: a front face; an array of optical display elements comprised within the front face; a plurality of fluid flow conduits, each conduit extending through the panel from an aperture on the front face; and a manifold in fluid communication with one or more of the plurality of fluid flow conduits, the manifold having one or more manifold inlets fluidly coupled to a fluid pump for displacing fluid through the conduits.

According to a second aspect, the present invention provides a visual display device including a visual display panel according to the first aspect, further comprising a controller for operating a controllable release of fluid from one or more fluid reservoirs through the conduits to the front face of the visual display panel.

According to a third aspect, the present invention provides a cartridge comprising one or more fluid reservoirs and being adapted for insertion into, and fluid connection with, a cartridge slot of a preferred embodiment of the visual display device of the second aspect.

Embodiments of the present invention will now be described by way of example and with reference to the accompanying drawings in which:

FIG. 3 is a schematic cross section and shows seven steps in a method of manufacturing the display panel of FIG. 2a;

Figure 1:
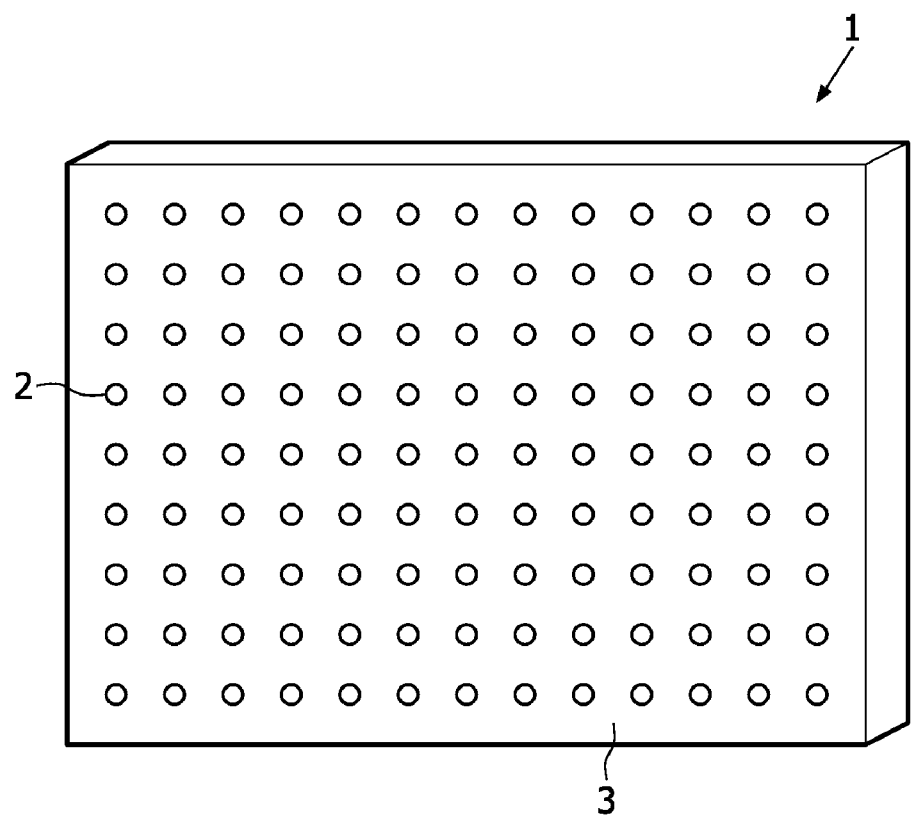
FIG. 1 shows a visual display panel according to an embodiment of the invention.

Referring to FIG. 1, a visual display panel 1 is shown in which a plurality of conduits 2 are provided in the form of an array. These conduits extend through the panel 1 from a front face 3.

Figure 2:
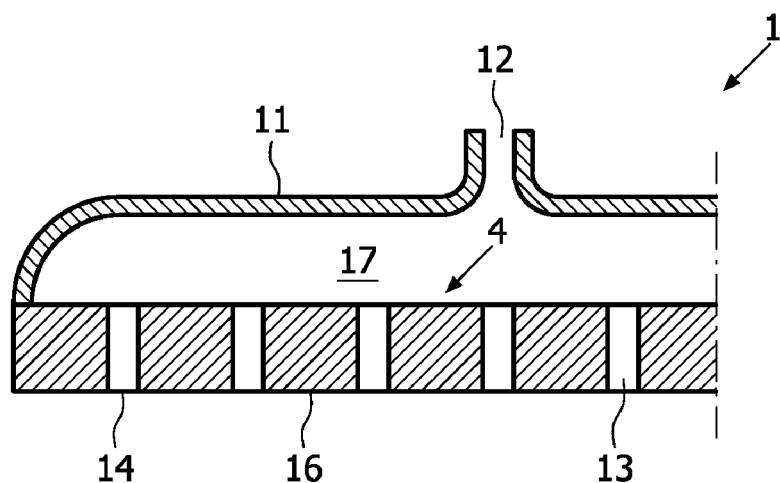
FIG. 2 shows a sectional view of a portion of a visual display panel of an embodiment of the invention.

FIG. 2 shows a partial sectional view through the panel 1 of FIG. 1, further illustrating a manifold 11 connected to a rear face 4 of the display panel 1. An array of optical display elements 16 is provided in the display panel 1. The manifold 11 extends over a number of the conduits 13, and forms a fluid connection between the conduits 13 and a manifold inlet 12. In use, fluid passes through the manifold inlet 12 into the manifold chamber 17, and thereby through the conduits 13, emitting through apertures 14 in the front face 3 of the panel 1. Plural manifolds may be provided to extend over all the conduits in the array.

Figure 4:
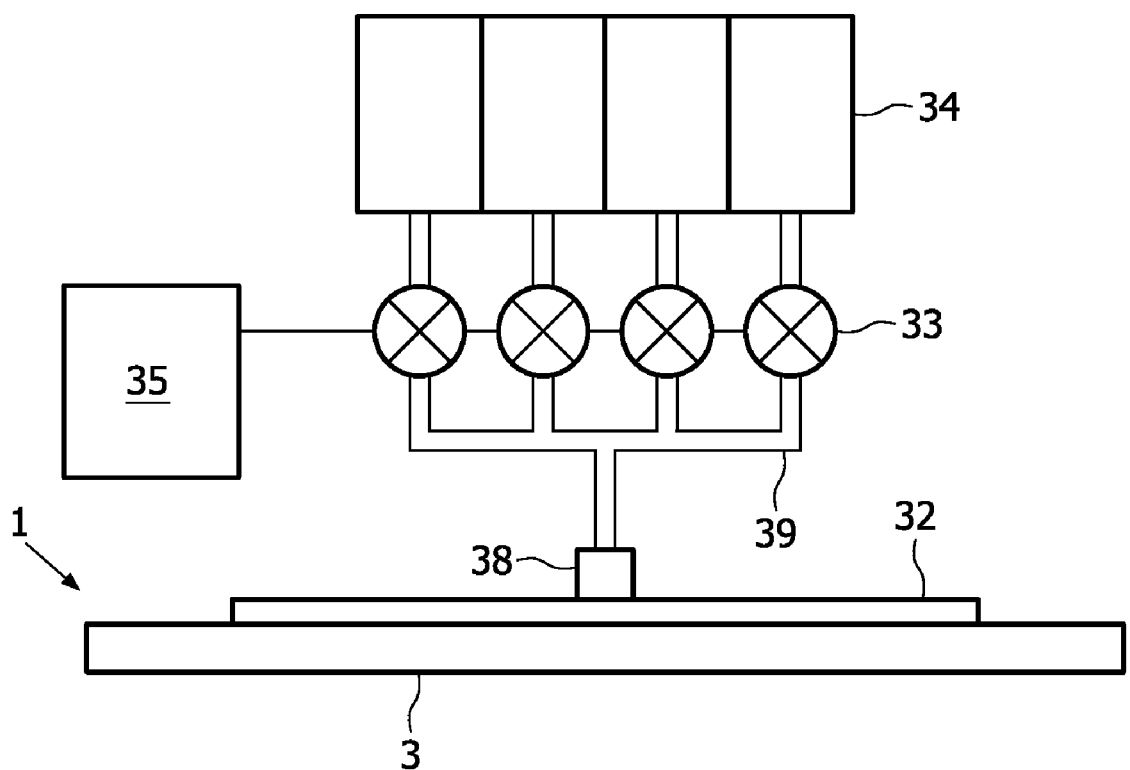
FIG. 4 shows a schematic diagram of an example assembly including a visual display panel of the invention.

The manifold may have a single inlet 12, connected via a single manifold connector 38, as shown in FIG. 4. Alternatively, the manifold or manifolds 32 may have a plurality of conduits, each of which are connected to a fluid reservoir 34 via a fluid pump 33.

The optical display elements 16 of the display panel may be of variable transmission type, such as in liquid crystal-based displays, or of variable emission-type, such as in light-emitting diode-based displays. Other types of flat panel displays may be suitably adapted for use with the invention. Examples of such displays are the above mentioned liquid crystal displays, field emission displays, electro-wetting displays, foil displays, polyled displays, fluorescent displays, touch-screen or pressure-sensitive displays and other types of display.

Figure 2A:
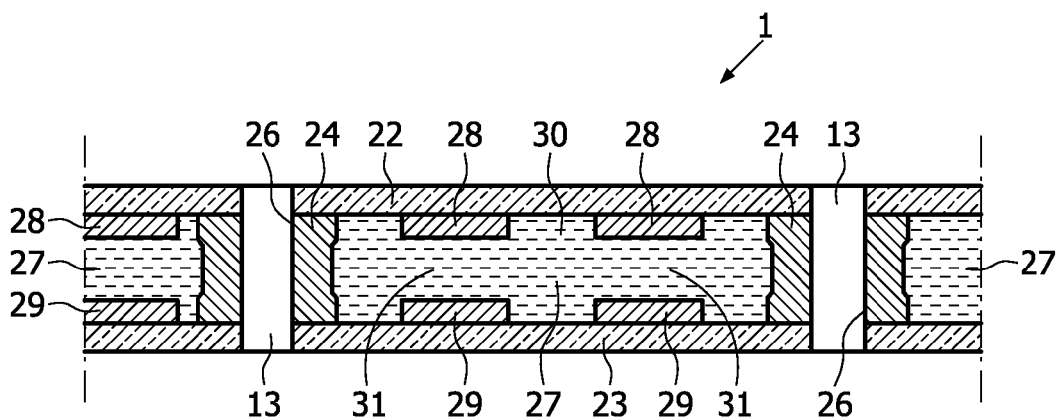
FIG. 2a is a cross section and shows a part of a display panel suitable for use with a first embodiment of the invention.
Figure 3A:
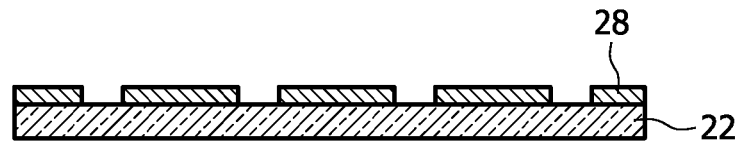
Figure 3B:
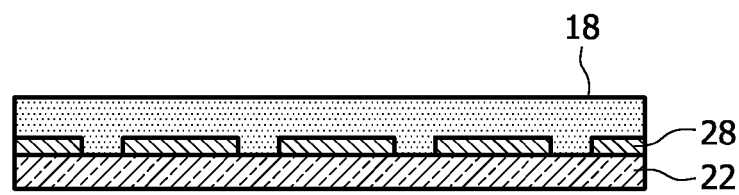
Figure 3C:
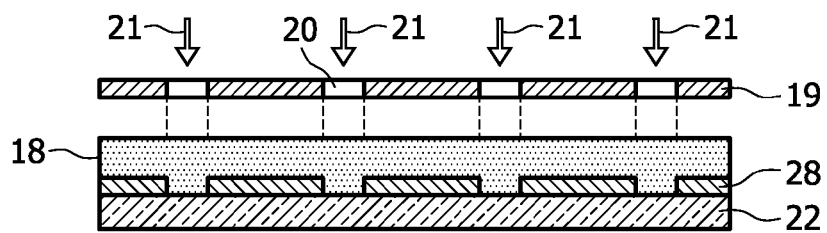
Figure 3D:
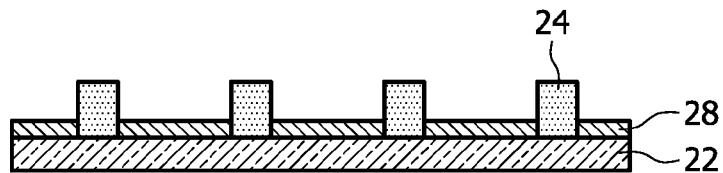
Figure 3E:
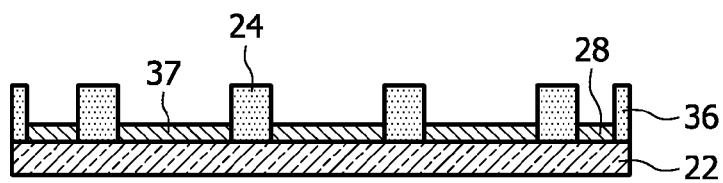
Figure 3F:
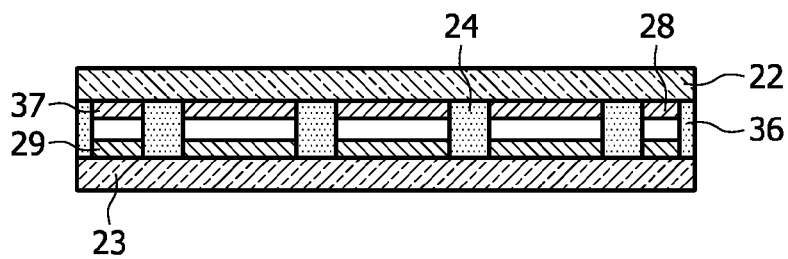
Figure 3G:
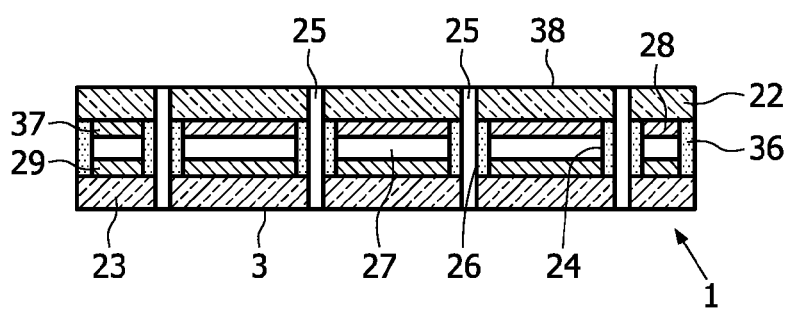

Indicated in FIG. 2a is a schematic section view of an example display panel suitable for use with the invention. The display panel 1 has a first substrate 22, which is made from a light-transmissive glass plate, and a second substrate 23, which may also be made of a light-transmissive glass plate. The two substrates 22, 23 are separated from each other by means of a plurality of spacers, of which two spacers 24 are shown in FIG. 2a. A conduit or through hole 13 has been formed in each spacer 24. The through hole 13 extends through both substrates 22, 23 and through the centre of the respective spacer 24. Each through hole 13 has a circumferential inner wall 26 which is formed by the substrates 22, 23 and the spacer 24. The wall 26 seals the through hole 13 from a space 27 formed between the substrates 22, 23.

The first substrate 22 is provided with a first set of light-transmissive electrodes 28, which could be made from ITO (Indium Tin Oxide) or another suitable material. The second substrate 23 is provided with a second set of light-transmissive electrodes 29, which could also be made of ITO. The space 27 between the electrodes is filled with a liquid crystalline material 30, based on the twisted nematic (TM), the supertwisted nematic (STN) or the ferroelectric effect so as to modulate the direction of polarisation of incident light. The sets of electrodes 28, 29 define between them a matrix of pixels 31. By controlling the voltage over each pixel 31 it is possible to display a desired image on the display panel 1.

FIG. 3 illustrates a method of manufacturing the display panel of FIG. 2a. The method includes photolithography for forming the spacers 24. In step (a) a set of light-transmissive electrodes 28 are provided on the first substrate 22. In step (b) a photosensitive polymer film 18, which could be an acryl-based negative resist, is provided on the first substrate 22.

Then, in step (c), a mask 19 having e.g. circular holes 20 is held above the film 18 at the same time as the film 18 is exposed to UV-radiation, represented by arrows 21. The UV radiation cures those parts of the film 18 that are exposed to the UV-radiation. After exposure to UV-radiation those parts of the film 18 that were shadowed by the mask 19 can, in step (d) be washed away by means of a suitable fluid leaving only the spacers 24 on the substrate 22. In step (e) a sealing strip 36 is attached to the first substrate 22 around its circumference. The first substrate 22 having the spacers 24 attached to one side 37 thereof is then, in step (f), put on the second substrate 23, having provided thereon the second set of electrodes 29, in such a way that the side 37 of the first substrate 22 faces the second substrate 23. A thin layer of glue has been provided on the top of each spacer 24 to assure a secure attachment to the second substrate 23.

Finally, in step (g), through holes 13 are drilled through each spacer 24 and the substrates 22, 23. The through holes 13 may be made by stamping, mechanical drilling, laser drilling, powder blasting, water jetting or any other method suitable for making through holes in the substrates 22, 23 and the spacers 24. The through holes 13 preferably extend in a direction being substantially perpendicular to the substrates 22, 23, i.e. perpendicular to the front face 3, being the surface on which the displayed image is to be viewed.

In FIG. 4 a schematic view of the relative arrangement of various components of an example display panel is shown, in which the display panel 1 has a manifold 32. Connected to the manifold 32 is a series of fluid pumps 33, fluidly connected to the manifold 32 via a distribution conduit 39 and manifold connector 38. Connected to each fluid pump 33 is a fluid reservoir 34.

A controller 35 is indicated, connected to each fluid pump in order to select and control the output from each fluid pump. The controller 35 provides a control signal to actuate each fluid pump appropriately so that controllable amounts of fluid from the fluid reservoirs 34 are injected into the manifold 32 via the distribution conduit 39 and manifold connector 38.

The fluid pump 33 may be a unit integral with the display panel, or it may be separable from it as a replaceable item. Preferably, the pump 33 and reservoir 34 are formed as a single replaceable unit, in a similar fashion to an inkjet cartridge for a printer. Replacement of the fluid once exhausted is then a matter requiring only a simple removal and reconnection of the pump and reservoir unit.

Further fluid pumps may be provided, which may together form an integrated multi-reservoir cartridge, or may be individually replaceable according to requirements and relative usage.

The fluid reservoir 34 may also be a replaceable item comprised within a cartridge containing one or more fluid reservoirs, either with or without an integral fluid pump 33.

One or more of the fluid reservoirs may be in the form of a pressurised gas cylinder that, in combination with other fluid reservoirs and fluid pumps, provide a means by which fluid is forced under pressure through the conduits 13 in the panel 1.

Certain types of fluids may be emitted in atomised or dispersed form, thus forming smoke-like emissions from the panel 1 in the form of, for example, a liquid-in-gas colloidal suspension.

The fluid to be pumped through the conduits 13 of the display panel 1 may be vaporised before entering the manifold. For example, if the fluid is supplied in the reservoir 34 in liquid form, a small amount of this liquid, when vaporised, will generate a much larger volume of vapour, which can then flow through the display panel. Vaporisation of the fluid may be achieved by means of a heating or atomising element within the pump assembly 33.

In use, the fluid pump 33 will, upon receiving a suitable control signal, pump a controlled quantity of fluid, which preferably comprises an odiferous compound. This odiferous compound is preferably dissolved in a carrier fluid. The compound is carried from the reservoir 34 through the manifold 32 and the panel 31. An odour is then detectable by a user.

A cartridge containing one or more reservoirs may be adapted to contain a range of different odiferous compounds. These compounds, when emitted singly or in combination from the apertures 14 on the front face 3 of the display panel 1 through the conduits 13 in the display panel 1, generate the required odour or combination of odours. The compounds may, in the reservoirs, be in either fluid (i.e. liquid or gaseous) form or in solid form. In solid form, for example as a wax, the fluid pump may comprise a heating element adapted to melt the solid material and subsequently pump the liquid or vapour thereby created through into the manifold 32, where the material generates the required odour through evaporation of the odiferous content of the material.

The term "fluid pump" as used herein is intended to encompass definitions which apply to pressure-operated valves which may conventionally be used for example in inkjet printing technology such as in electrostatic, thermal, electromagnetic, piezoelectric or other printheads. The term also encompasses valves being operated in conjunction with pressurised fluid reservoirs, in which fluid is pumped through the valve under pressure when the valve is in the open position.

A further fluid pump may alternatively or in addition be provided which is capable of forcing air through the conduits in either a forward or reverse direction. This further fluid pump is preferably in the form of a fan, and is preferably able to operate in either direction. This fan may usefully have the function of, in the forward direction, removing dust from the screen or clearing the manifold and conduits of odiferous fluid and, in the reverse direction, drawing air and thus removing odour and small airborne particles from the atmosphere in which the display panel is situated.

Figure 5:
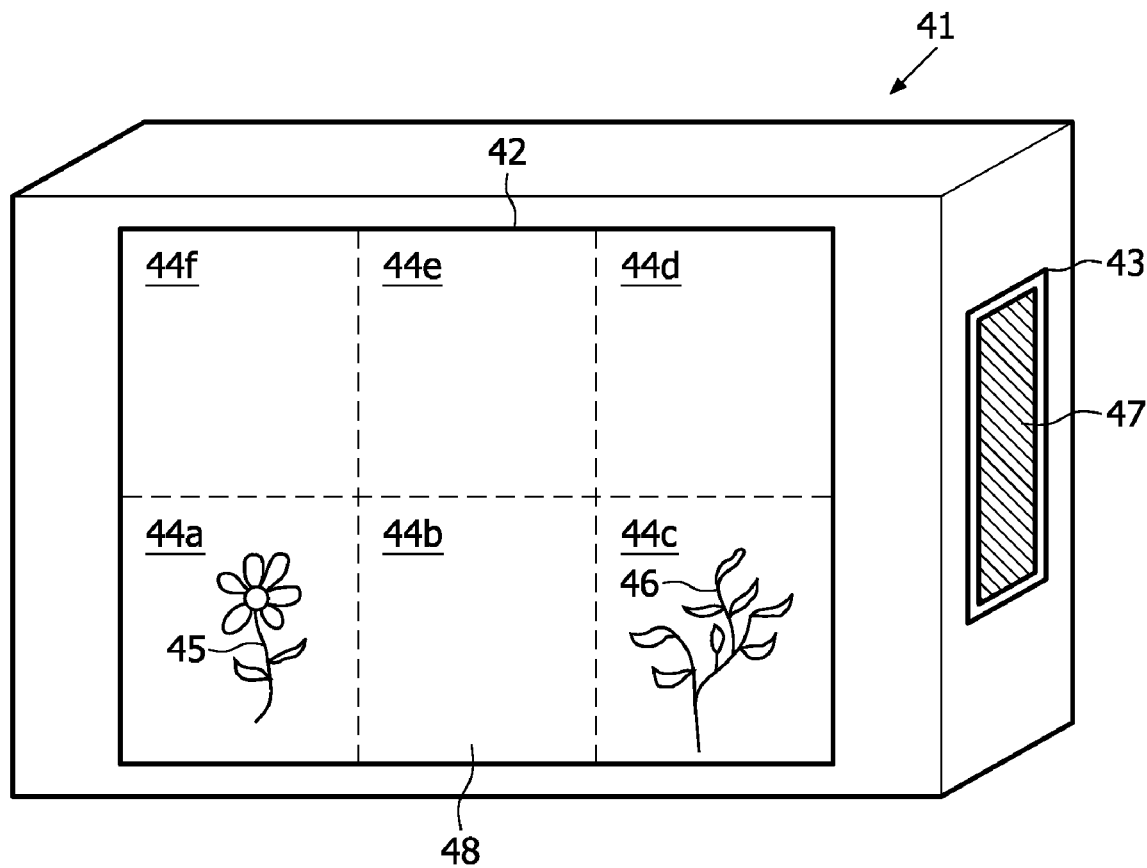
FIG. 5 shows a view of a particular embodiment of the invention, comprising a touch screen display panel within a visual display device.

Referring to FIG. 5, a visual display device 41 is illustrated incorporating a visual display panel 42. This visual display panel 42 is provided with a touch-sensitive front face 48 which, in this example, is subdivided into various sectors 44a-44f. Presented on the panel 42 are images 45, 46. The visual display device 41 is configured such that when a user touches a region 44a corresponding to a relevant image 45, a predetermined odour is emitted from the front face of the panel. This odour may be emitted from the front face 48 in general or from a corresponding portion 44a on the front face 48.

For example, a user may press on a certain location on the front face of the panel 42 to cause a certain type of odour to be emitted. Odours from different herbs 46 or flowers 45 may thereby be spread over different regions 44c, 44a of the panel 42. These odours may also be released in time sequential or in simultaneous fashion with or without input from a user. A user of the visual display device 41 would then be able to associate the smell of a particular region 44a of the panel 48 with the image 45 displayed thereon.

A cartridge slot 43 is shown in the visual display device 41 of FIG. 5. This cartridge slot is shaped to receive a cartridge 47 comprising one or more fluid reservoirs 34. Inserting the cartridge 47 creates a fluid connection between the one or more fluid reservoirs and the manifold 32 within the visual display device, via one or more fluid pumps 33.

Figure 6:
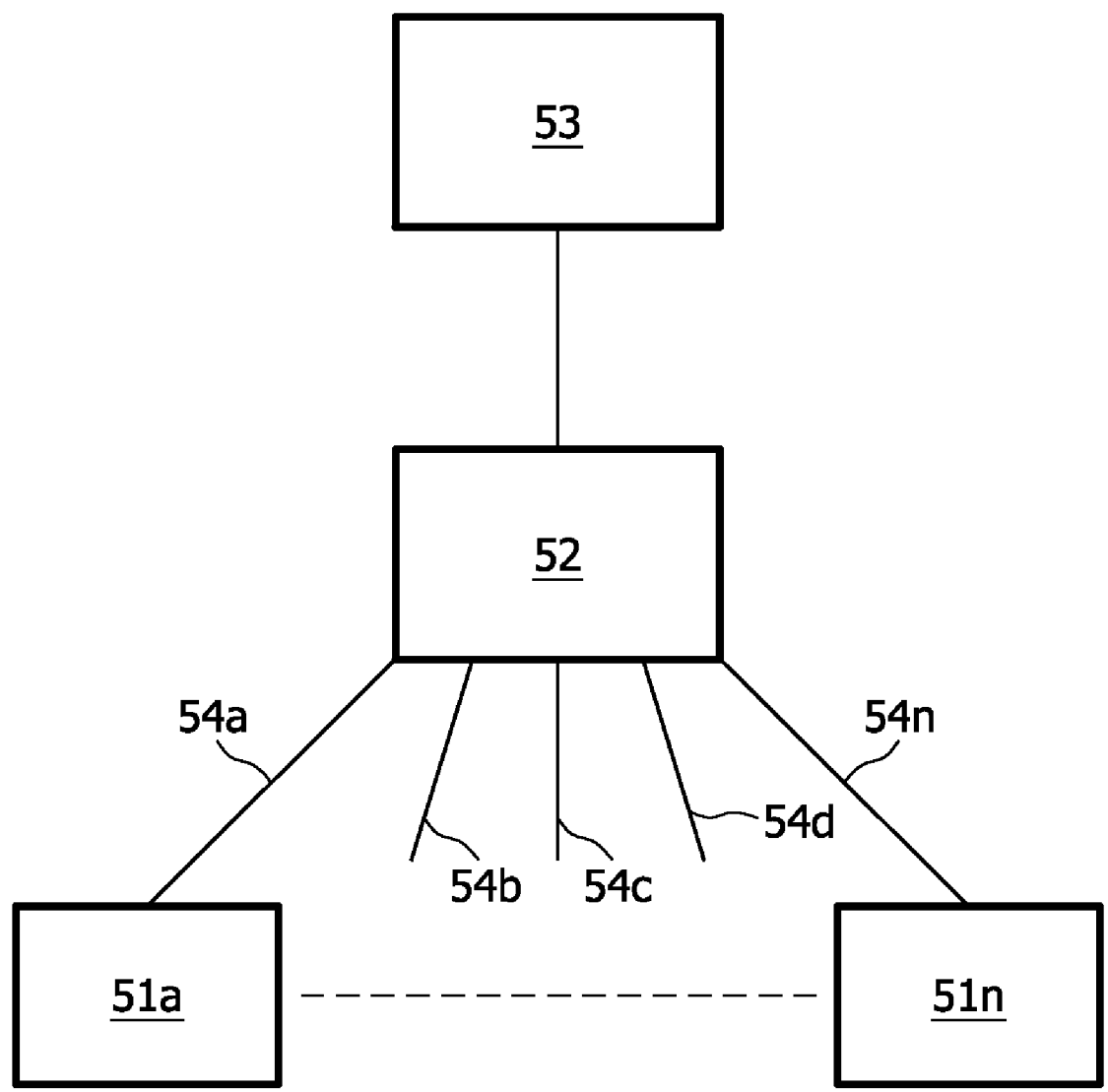
FIG. 6 shows schematically a networking arrangement for a plurality of visual display devices of an embodiment of the invention.

Referring to FIG. 6, a schematic networking arrangement is illustrated in general form for a number of individual visual display devices 51a-n of an embodiment of the invention. Each visual display device 51a-n is connected to a network transmission medium 52 via communication links 54a-n. The transmission medium 52 may be in the form of an electronic network such as an intranet or internet, a cable television network, a satellite link, a terrestrial broadcast network or similar. The transmission medium 52 may be one-way, i.e. receive only, or two-way, i.e. each visual display device being able to both transmit and receive. Transmissions from a service provider 53 may be received on each visual display device 51a-n. These transmissions may be in the form of audio and video data, and may additionally include information relating to the odiferous content of the transmission. A suitably configured visual display device 51a will be able to produce an odour corresponding to the odiferous content of the transmission at an appropriate point in the transmission.

For example, if the service provider is a television broadcaster or internet site, advertising included in a broadcast or webpage can include odiferous information content to which a suitably configured visual display device 51 can respond. Interactive content can also be provided, for example where a user is requested to touch the screen at an appropriate place and/or time, to cause the visual display unit to emit a predetermined odour or combination of odours.

The transmission from the service provider 53 may be in the form of a broadcast, i.e. a "one to many" simultaneous transmission, or individually and asynchronously, i.e. "one to one". Additionally, in the case of a two-way communication links 54a-n, a user operating a visual display device 51a is able to communicate with another user 51n, or possibly more than one user, via the communication medium 52. Information comprising audio, visual and odiferous content may be transmitted between the users.

In examples of two-way communication, an audio and/or visual interaction between two users on separate visual display devices 51, 51n can be complemented via odiferous content transmitted between the users. An interactive multi-player gaming environment, for example, can be thereby enhanced. A remote consultancy, such as aromatherapy, may be possible when odiferous content is transmitted to one or more users equipped with a visual display device of a preferred embodiment of the present invention.

In computer video games, the addition of odiferous information can add a further dimension to the playability of a game. A player may be guided by particular smells in certain virtual locations of the game, for example in an immersive 3-D environment.

In another embodiment, the visual display device 41 may be adapted to be worn by a user. This may be in the form of a wearable screen adapted to be attached to clothing. For example, by means of further through holes situated around the edge of the screen, the screen can be attached to a fabric substrate by stitching. Alternatively, with the visual display device 41 sized to fit a virtual 3-D headset, a "virtual reality" experience may incorporate odiferous information content as well as visual and audio information, which can further enhance the immersive experience.

Odours emitted by the visual display device are not necessarily consciously detectable by a user, but can be mood-altering substances such as pheromones or medicinal treatments such as drugs.

Other embodiments are intentionally within the scope of the appended claims.

The invention claimed is:

1. A visual display panel comprising:
a panel having a front face and a rear face, wherein the panel further comprises a first substrate, a second substrate, and a plurality of spacers separating the first and second substrates from each other;
an array of optical display elements within the panel;
a plurality of fluid flow conduits formed in the plurality of spacers, each conduit extending through both the first and second substrates and through a center of a respective spacer of the panel from an aperture on the front face; and
a manifold in fluid communication at the rear face of the panel with one or more of the plurality of fluid flow conduits,
the manifold having one or more manifold inlets fluidly coupled to a fluid pump for displacing fluid from the one or more manifold inlets through the plurality of fluid flow conduits, and emitting the fluid through the apertures on the front face of the panel.

2. The visual display panel of claim 1, wherein the fluid pump is fluidly coupled to a fluid reservoir.

3. The visual display panel of claim 1, wherein the fluid pump comprises a valve.

4. The visual display panel of claim 1, wherein the fluid pump comprises an electrostatic, thermal, electromagnetic or piezoelectric device.

5. The visual display panel of claim 1, wherein the fluid pump comprises a fan for forcing gas through the fluid flow conduits in the panel.

6. The visual display panel of claim 1, further comprising one or more touch sensitive elements on the front face of the panel.

7. A visual display device including a visual display panel according to claim 1, further comprising a controller for operating a controllable release of fluid from one or more fluid reservoirs through the plurality of fluid flow conduits to the front face of the panel.

8. The visual display device of claim 7 adapted to be connectable to a communications network, through which network is transmitted odiferous information content for receipt by the visual display device, wherein the visual display device produces an odour corresponding to the odiferous information content.

9. The visual display device of claim 7, further comprising a cartridge slot adapted to receive and fluidly connect to a cartridge containing a fluid reservoir.

10. The visual display device of claim 7 adapted to be worn by a user.

11. A cartridge comprising one or more reservoirs and being adapted for insertion into, and fluid connection with, the cartridge slot of claim 9.

12. The cartridge of claim 11, wherein the one or more reservoirs each contain an odiferous compound.

13. The cartridge of claim 11, wherein the one or more reservoirs are fluid reservoirs.

14. The cartridge of claim 13, further comprising one or more fluid pumps in fluid communication with the one or more fluid reservoirs.

* * * * *